US012004526B2

(12) United States Patent
Lam et al.

(10) Patent No.: US 12,004,526 B2
(45) Date of Patent: Jun. 11, 2024

(54) DEVICE AND METHOD FOR HERBS DISINFECTION BY PLASMA (71) Applicant: NOVAGREEN TECHNOLOGIES LTD., Kibbutz Megiddo (IL)

(72) Inventors: Amnon Lam, Kibbutz Givat Oz (IL); Aviad Harhol, Ramat Hasharon (IL); Doron Shuster, Tel Adashim (IL); Betsalel Rechav, Ness Ziona (IL)

(73) Assignee: NOVAGREEN TECHNOLOGIES LTD., Kibbutz Megiddo (IL)

( * ) Notice: Subject to any disclaimer, the term of this patent is extended or adjusted under 35 U.S.C. 154(b) by 224 days.

(21) Appl. No.: 17/423,300

(22) PCT Filed: Jan. 23, 2020

(86) PCT No.: PCT/IL2020/050092
§ 371 (c)(1),
(2) Date: Jul. 15, 2021

(87) PCT Pub. No.: WO2020/152685
PCT Pub. Date: Jul. 30, 2020

(65) Prior Publication Data
US 2022/0095637 A1 Mar. 31, 2022

(30) Foreign Application Priority Data
Jan. 24, 2019 (IL) .......................................... 264463

(51) Int. Cl.
*A61L 2/00* (2006.01)
*A23B 7/144* (2006.01)
(Continued)

(52) U.S. Cl.
CPC .............. *A23B 7/144* (2013.01); *A23L 3/001* (2013.01); *A23L 3/003* (2013.01); *A23L 3/015* (2013.01);
(Continued)

(58) Field of Classification Search
CPC .... A61L 2/00; A61L 2/208; A61L 2/20; B01J 19/08; A23B 9/22
(Continued)

(56) References Cited

U.S. PATENT DOCUMENTS 6,543,460 B1 4/2003 Denes
8,771,595 B2 7/2014 Paskalov
(Continued)

FOREIGN PATENT DOCUMENTS

CA    2827119 A1    8/2012
CN    204158755 U   2/2015
(Continued)

OTHER PUBLICATIONS

Betts (2014) Microbial update—herbs & spices. International Food Hygiene 25(1); pp. 9 and 11.
(Continued)

*Primary Examiner* — Monzer R Chorbaji
(74) *Attorney, Agent, or Firm* — Dorsey & Whitney LLP (57) ABSTRACT Device and method suitable for disinfecting herbs using plasma are disclosed. The device comprises a chamber and two sets of electrodes in an opposed position one relative to the other, inside the chamber. Each electrode in one set has a counterpart electrode in the other set, the two electrodes positioned facing each other and being configured to connect to a RF HV power supply, to produce a plasma-generating EM field in the space between the electrodes. The device further comprises a dielectric carrier positioned inside the chamber in the space between the two sets of electrodes, the carrier being dimensioned and configured to carry herbs in granular form such as powder or particles thereon. A portable sealable container comprising a unidirectional valve is also disclosed, configured to store herbs thereinside during plasma treatment in the device, and to store the disinfected (Continued)

herbs after treatment under vacuum. A device for disinfecting herbs by evaporating a disinfection agent in an evacuated chamber is also disclosed where plasma is used in any of several methods to enhance, improve and expedite the disinfection process.

16 Claims, 3 Drawing Sheets

(51) Int. Cl.
*A23L 3/00* (2006.01)
*A23L 3/015* (2006.01)
*A23L 3/3409* (2006.01)
*A61L 2/14* (2006.01)
*B01J 19/08* (2006.01)
*H01J 37/32* (2006.01)

(52) U.S. Cl.
CPC ......... *A23L 3/34095* (2013.01); *A61L 2/0094* (2013.01); *A61L 2/14* (2013.01); *H01J 37/32* (2013.01); *A23V 2002/00* (2013.01); *A61L 2202/122* (2013.01)

(58) Field of Classification Search
USPC .................................................. 422/23, 186
See application file for complete search history.

(56) References Cited

U.S. PATENT DOCUMENTS

| | | | |
|---|---|---|---|
| 2006/0257280 | A1 | 11/2006 | Hammerstrom |
| 2010/0028200 | A1* | 2/2010 | Shiosawa ............... A61L 2/208 422/23 |
| 2014/0023554 | A1 | 1/2014 | Paskalov |
| 2015/0101082 | A1 | 4/2015 | Bormashenko |
| 2015/0209462 | A1 | 7/2015 | Turbett |
| 2015/0373923 | A1 | 12/2015 | Ferrell |
| 2016/0227699 | A1 | 8/2016 | Wolfe |
| 2017/0000167 | A1 | 1/2017 | Corrigan |
| 2017/0112157 | A1* | 4/2017 | Keener ..................... A61L 2/20 |

FOREIGN PATENT DOCUMENTS

| | | |
|---|---|---|
| CN | 104584728 A | 5/2015 |
| CN | 204671610 U | 9/2015 |
| DE | 10036550 A1 | 9/2001 |
| DE | 102009025864 A1 | 10/2010 |
| EP | 1192953 B1 | 7/2011 |
| EP | 3085244 A1 | 10/2016 |
| IL | 259283 | 11/2019 |
| JP | 2017086705 A | 5/2017 |
| KR | 20120005723 U | 8/2012 |
| KR | 20130128915 A | 11/2013 |
| KR | 20140002357 A | 1/2014 |
| KR | 20170050258 A | 5/2017 |
| NL | 1033408 C2 | 8/2008 |
| PL | 405861 A1 | 5/2015 |
| PL | 408384 A1 | 12/2015 |
| PL | 415215 A1 | 6/2017 |
| WO | 0201971 A1 | 1/2002 |
| WO | 2010016347 A1 | 2/2010 |
| WO | 2012112042 A1 | 8/2012 |
| WO | 2015059702 A1 | 4/2015 |
| WO | 2016140447 A1 | 9/2016 |
| WO | 2016190436 A1 | 12/2016 |
| WO | 2019215741 A1 | 11/2019 |

OTHER PUBLICATIONS

Chingsungnoen et al., (2018) Antimicrobial Treatment of *Escherichia coli* and *Staphylococcus aureus* in Herbal Tea Using Low-Temperature Plasma. J Food Prot 81(9): 1503-1507.

Hertwig et al., (2015) Impact of remote plasma treatment on natural microbial load and quality parameters of selected herbs and spices. Journal of Food Engineering 167(Part A): 12-17.

Hertwig et al., (2018) Cold atmospheric pressure plasma and low energy electron beam as alternative nonthermal decontamination technologies for dry food surfaces: A review. Trends in Food Science & Technology 77: 131-142.

Hong et al., (2009) Sterilization effect of atmospheric plasma on *Escherichia coli* and *Bacillus subtilis* endospores. Lett Appl Microbiol 48(1): 33-37.

Kim et al., (2014) Microbial decontamination of red pepper powder by cold plasma. Food Microbiology 38: 128-136.

Man et al., (2016) Health Threats from Contamination of Spices Commercialized in Romania: Risks of Fungal and Bacterial Infections. Endocr Metab Immune Disord Drug Targets 16(3); 8 pages.

Pauly and Paszkiewicz (2011) Cigarette smoke, bacteria, mold, microbial toxins, and chronic lung inflammation. J Oncol 2011: 819129; 14 pages.

Promping et al., (2019) Efficacy of DBD Plasma Generator with Different Shapes and Materials of Electrodes for Reducing the Microbial Contamination of Herb Powder. Walailak J Sci & Tech 16(6): 415-422. Presented at the 10th International Conference on Plasma Science and Applications 2017: Oct. 10-11, 2017.

Ruchlemer et al., (2015) Inhaled medicinal cannabis and the immunocompromised patient. Support Care Cancer 2(3): 819-822.

CeraPlas™ piezo plasma generator; Cold plasma from a single component [Oct. 31, 2014]. Retrieved from: https://www.tdk-electronics.tdk.com/en/373562/tech-library/articles/applications-cases/applications-cases/cold-plasma-from-a-single-component/1109546, on Nov. 11, 2020. 6 pages.

Piezoelectric Transformer, Inverter Module; Multi-layered Rosen Type Transformer. Nihon Ceratec Co., Ltd. Retrieved from: http://www.ceratecinc.com/pdf/transformer/PiezoelectricTransformer_InverterModule.pdf, on Nov. 17, 2020; 6 pages.

\* cited by examiner

DEVICE AND METHOD FOR HERBS DISINFECTION BY PLASMA

CROSS-REFERENCE TO RELATED APPLICATIONS

This application is a U.S. Nationalization of PCT International Application No. PCT/IL2020/050092 filed on Jan. 23, 2020, which claims priority to Israel Patent Application No. 264463 filed on Jan. 24, 2019.

FIELD OF THE INVENTION

The invention, in some embodiments, relates to the field of disinfection of herbs by plasma.

BACKGROUND OF THE INVENTION

Plasma refers herein to ionized fluid, including positively charged ions and negatively charged electrons, wherein the whole volume of the ionized fluid is roughly neutral. Positively charged ions and negatively charged electrons are generally referred to herein as "ions" and "electrons" respectively. Neutral atoms and molecules are referred to as "neutrals". Non-thermal (or "cold") plasma refers to plasma wherein the neutrals' temperature, dictated by the neutrals' average random velocity, is low, e.g. below about 55 degrees C. or even below about 40 degrees C.

Herbs herein may include any product from plants in the form of granular material including small pieces, particles or even powder, and are meant to include spices. Such herbs may be produced from various parts of the plant—alone or mixed together in combinations—such as from leaves or stems; from flowers, grains or seeds; from fruits and berries, roots or bark etc. These may possibly be chopped to pieces, crushed or grinded or powdered. Before or after such chopping or grinding etc., the herbs may be processed e.g. by backing or drying or any other processing. The herbs may be provided and/or consumed relatively fresh, within hours or days after harvesting, or, additionally or alternatively, may be supplied and/or consumed weeks or months after harvesting (consuming herein includes eating, drinking, smoking, inhaling and any other way of exploiting and consuming the herbs for personal use). Herbs may possibly (but not necessarily) be consumed after being processed, for instance to facilitate packaging, or preservation or consuming etc. Such processing prior to consuming (performed either by a manufacturer or a supplier or the consumer) may include for instance any one or a combination of drying, baking, cooking, grinding or crushing—to name a few.

Recognition of hazardous infectious bacteria and fungi on herbs have grown considerably in recent years. Betts (International Food Hygiene, Vol. 25 No. 1 (2015) P 11, http://www.positiveaction.info/pdfs/articles/fh25_1p9.pdf) quotes a report to the UK Advisory Committee on the Microbiological Safety of Foods in 2008, reporting that the *Salmonella* contamination rate of dried herbs and spices could be between 0.6% and 14%, with UK samples being contaminated at a rate of 1%. In further surveys conducted in the USA, the FDA sampled 2,844 imported dry spice shipments from 2007 through 2009 and found about 7% contained *Salmonella*, twice the rate of other FDA regulated food products. Betts concludes that due to their methods of production, herbs and spices are often contaminated with a wide variety of micro-organisms, some may be considered human pathogens.

Man et. al. ("*Health Threats from Contamination of Spices Commercialized in Romania: Risks of Fungal and Bacterial Infections*", Endocr. Metab. Immune Disord. Drug Targets. 2016, 16(3), 197-204) found that fungi were observed in 72.7% of black pepper samples, 33.3% in white pepper, 30% in sweet chili and 25% in hot chili products. The most common isolated fungus was *Aspergillus* spp., while *Rhizopus, Mucor, Fusarium, Penicillium* and *Absidia* species were also found in smaller percentage.

In a review study regarding tobacco ("*Cigarette Smoke, Bacteria, Mold, Microbial Toxins, and Chronic Lung Inflammation*", Journal of Oncology Volume 2011 (2011), Article ID 819129), Pauly and Paszkiewicz argue that tobacco companies have identified and quantified bacteria, fungi, and microbial toxins at harvest, throughout fermentation, and during storage. Yet, the authors also note that ample information has accumulated to suggest that microbes and microbial-derived factors may contribute to the health risks of smoking and smokeless tobacco products. Moreover, the microbes may facilitate microbial colonization of the mouth and airway, the induction of chronic inflammation through the activation of diverse leukocyte subsets, alteration of the tissue microenvironment, and microbial-toxin-induced pathologies. The authors conclude that tobacco products should be assessed with the knowledge that they contain bacteria, mold, and microbial toxins.

The case of cannabis is particularly important, because medical cannabis is often recommended or even prescribed to people in various stages of compromised health, that might therefore be more vulnerable than healthy people to pathogens. Ruchlemer et. al. ("*Inhaled medicinal cannabis and the immunocompromised patient*", Support Care Cancer (2014), DOI 10.1007/s00520-014-2429-3) list some 10 references describing the detrimental effects of inhaled *Aspergillus* via cannabis among patients, most of whom were immunocompromised. In some of those cases, the outcome was fatal. The research aimed to identify the safest way of using medicinal cannabis in immunosuppressed patients by finding the optimal method of sterilization with minimal loss of activity of cannabis. The authors have found plasma sterilization to be effective and causing the least quantitative loss of the active cannabis compound $\Delta 9$-THC, and argue that systematic sterilization of medicinal cannabis can eliminate the risk of fatal opportunistic infections associated with cannabis among patients at risk.

Plasma-assisted sterilization (e.g. of medical instruments or food packages) is known, and is typically characterized by sterilizing at low temperatures objects that could be damaged by high temperature sterilization processes such as steam sterilization for example. Typical low-temperature plasma sterilizers employ hydrogen peroxide ($H_2O_2$) as a precursor for the active species. $H_2O_2$ may be added to the plasma chamber in a liquid form and following evaporation and diffusion in the space of the chamber, plasma-induced ions and free radicals originating from the $H_2O_2$ employ the organisms extermination. However, such use of plasma-assisted $H_2O_2$ sterilization is regulated and restricted in many countries of the world in terms of the objects that may be sterilized, the concentrations allowed to be used and the means and time that should be applied after such employment so as to verify sufficient disintegration to prevent health risks for a user. Thus, such sterilization processes that employ hydrogen peroxide may be considered less than optimal or even prohibited for sterilizing food or herbs in some countries.

Some additional solutions have been proposed to sterilize food powder using plasma. U.S. Pat. No. 8,771,595 discloses systems and methods for plasma sterilization wherein the method includes placing a substance to be sterilized in a rotating chamber (e.g., drum) and exposing the substance to a radio frequency (RF) plasma. The mixing of the substance and plasma is further promoted by generating a magnetic field that produces a force on the substance in a direction opposite to the rotational direction of the chamber.

SUMMARY OF THE INVENTION

Some aspects of the invention relate to disinfection of herbs by plasma, and more specifically but not exclusively, to devices and methods for disinfecting herbs in medium quantities, e.g. quantities suitable for the retailer.

Disinfecting food, and particularly disinfecting herbs, is different in several aspects from disinfecting inanimate articles (such as, for example, medical devices). Food and herbs are much more sensitive and can be easily modified or damaged or even disintegrated, if subjected to typical sterilization procedures that are suitable for items made of plastics, glass or metal, e.g. processes that involve high temperatures and/or high pressure. Radiation-based techniques (e.g. gamma-ray radiation) may also be inadequate or less than optimal for food, because the radiation might also damage the food, and because this technique is more expensive than alternative ones. Using disinfectants is also very limited or totally prohibited, because disinfectants might be adsorbed or absorbed in the food and practically impossible to remove to a sufficient degree after applying.

In contrast to the above-described methods, cold plasma may be highly effective in disinfecting herbs, while preserving all or at least most of the herbs characteristics and ingredients. In the study quoted above, Ruchlemer et. al. have demonstrated that using cold plasma was very effective in disinfecting cannabis herbs, while causing the least quantitative loss of the active cannabis compound Δ9-THC. Generally, disinfection is effected due to active molecules that are generated during ionization of an oxygen-containing gaseous composition, for example low-pressure air, and due to such molecules' destructive effect on living organisms. Such active molecules or atoms may include for example NO, O, CO, and others. Optionally, plasma ignition may be facilitated if additional gases, for example inert gases such as helium or argon, are added to the composition. If He is introduced to the gaseous mixture, then excited He may also be found in the gas following ionization. Moreover, if sources of hydrogen atoms are present—for example if the ionized gas includes water vapor—then H and OH— may also be found following ionization, potentially providing for enhanced disinfection effectiveness. Experiments, some of which are detailed further below, show that exposure of herbs infected by bacteria or fungi to the active gaseous mixture obtained following plasma generation as described herein, results in extermination or at least substantial reduction of the infectious species and hence disinfects the herbs. Required exposure duration is less than 30 minutes, typically less than 10 minutes, and in some cases even less than 5 minutes. It is noted that introduction of hydrogen peroxide (H2O2) related additives to the gaseous mixture prior to plasma generation may in some embodiments enhance and expedite the extermination of bacteria and fungi; however in preferred embodiments, satisfactory disinfection may be obtained without such introduction of H2O2-related additives.

Generally, disinfecting an object by plasma may be carried out according to two different schemes. In one scheme (termed here "indirect") the plasma is generated (that is to say the gas is ionized) in one region while the object to be treated is positioned in a different region, where ionization does not occur. According to this scheme, gas is either made to flow, or allowed to diffuse, from the region of ionization to the region where the treated object is located. According to the second scheme (termed here "direct"), the object to be treated is positioned substantially within the region where ionization takes place, e.g. in a region between two or more electrodes where an electric or electromagnetic field is applied to ionize the gas. The two described schemes have different characteristics, and from a practical point of view, each has some advantages (and obviously disadvantages) relative to the other.

It is first noted that ionized gas includes various types of active species having, generally, various time constants for decay. For example, positively charged ions and negative charge electrons, generated by the excitation and ionization of initially neutral atoms and molecules, may recombine over a time scale shorter than a millisecond, e.g. on the order of magnitude of microseconds. Likewise, relaxation of excited atoms and molecules typically occur over time scales shorter than milliseconds. Recombination of electrons and ions, as well as relaxation of excited atoms and molecules, typically involve emission of light, hence the region where recombination and relaxation occurs is typically characterized by light emission (glow). After recombination and relaxation, the gas that was ionized may generally include also active species—predominantly active molecules—which recombine or decay or decompose over times longer than recombination and relaxation times, e.g. up to an order of magnitude of seconds or more, such as some types of free radicals. Thus, when plasma is generated at a distance from a region to be treated, and then guided towards that region, only active species that decay over relatively long times may survive the travel and affect the treated region. Species with decay times shorter than the travel time from the plasma generation region to the treatment region may decay during the travel, and consequently may not contribute to treatment.

Thus, applying a direct scheme of plasma treatment, namely generating plasma around or in the immediate vicinity of the treated object or material, provides an excess of highly excited species—including ions and electrons—in the immediate vicinity of the object's surface. Consequently, the effects on the objects surface are typically more intense and evolve faster in the direct scheme.

However, in the direct scheme, the treated herbs are subjected to the plasma-generating EM field, and consequently to the bombardment of the charge carriers in the plasma. In other words, the herbs treated in the direct scheme may be at risk, in some cases, of being damaged due to either the EM field or the ion bombardment, or even both. The direct exposure to varying EM fields, typically at radio frequencies, may excite molecular or atomic degrees of freedom in the treated herbs, thereby generating heat exceeding in some cases the temperature of the plasma itself. In some cases electric currents may be induced in the herbs, which may also generate heat or adversely affect some of the herbs qualities. Moreover, ion bombardment may damage the herbs external surface or even cause chemical transformations or leave contamination residues thereon.

Furthermore, generating plasma in the immediate vicinity of herbs, e.g. in the form of small pieces or powder, may be unpredictable in some cases, difficult to employ, or impossible altogether. Since plasma generation—gas ionization—in a given region is achieved by applying strong electric or electromagnetic (EM) fields across that region, any object placed in the effected region may alter the fields, sometimes in unpredictable manners. For example, the effect of a pile of herbs placed in between two electrodes applying a plasma-generating EM field therebetween, may depend on a combination of factors, including for example the size and shape of the pile of herbs and the exact location thereof relative to the electrodes, the dimensions of the pieces or particles that make up the pile, the air gaps between the particles, and the electrical conductivity of the particles, just to name a few such factors. For example, two samples of the same herb that are similar in overall quantity and sizes, but having different levels of moisture (e.g. one sample is dried and the other is not)—may cause very different results when placed in a region where plasma-generating EM field is applied. In some cases, for example, the moist powder will facilitate arcing, forming together a high conductivity trajectory between electrodes, and thereby prevent the formation of stable glow discharge, that may be required for the desired plasma generation. As another example, two samples of the same herb and in similar quantities, may also cause very different behavior of plasma, if one sample is treated while being placed still as a pile, whereas the other sample is treated while being maintained floating in the space between the electrodes (e.g. by a mixer or a fan).

Accordingly, an indirect scheme, wherein plasma is generated distantly from the treated material, typically (however not necessarily) offers a safer and more predictable working point compared to the direct scheme. Because the plasma is generated in a region void of the treated material, plasma generation is typically dependent only on the operational parameters (such as the spatial arrangement and geometry of the electrodes and electromagnetic power and frequency supplied to the electrodes), and hence is more easily predictable and controllable. Moreover, because the treated herbs are not directly subject to the plasma-generating EM field, field-induced damage and ion bombardment on the herbs surfaces are prevented. However a possible downside of the indirect scheme, is that after ionization the excited gas must be directed or allowed to flow or to diffuse towards the treated material. Consequently, some of the excited molecules and active species decay during the travel as explained above, resulting in exposure of the treated material to a smaller variety and smaller concentration thereof, ultimately resulting in a possibly less intense treatment, compared to the direct scheme.

It may therefore be concluded that selecting the direct scheme or the indirect scheme may be dependent on several factors, some of them may be gained or clarified through trial and error. It is typically expected that the direct scheme may provide a more intense—and hence a faster—process, but may involve a higher likelihood—risk—of damage to the treated herbs, or unpredicted results, or may be impossible to implement. It is further concluded that if the indirect scheme is adopted, the closer the plasma generation region is to the location of the treated material, the higher the effectiveness of the treatment is expected to be.

There is therefore provided, according an aspect of the invention, a device for disinfecting herbs using plasma, wherein the device comprises a sealable plasma chamber and a carrier made of a dielectric material, configured to contain the herbs during the treatment, inside the chamber. The plasma chamber may be fluidly associated with a vacuum pump, configured to evacuate the plasma chamber to a sub-atmospheric pressure. Two sets of electrodes, each set having one electrode or more, are arranged on opposing sides of the carrier, so that the herbs are located in a space between the electrodes of one set and the electrodes of the other set. At least one insulator layer is located between the herbs and at least one set of the electrodes so that the plasma is excited in a dielectric barrier discharge (DBD) mode of operation. In some embodiments the dielectric carrier may function as such an insulator layer. According to some embodiments, a second insulator layer is located between the herbs and the other set of electrodes, so there are two dielectric barriers between the sets of electrodes. The electrodes are associated with one or more RF HV power sources so that each power source is associated with two opposing electrodes in the two sets, for delivering to the electrodes a RF HV, for producing a plasma generating EM field in the space between the two opposing electrodes. In some embodiments the power to the electrodes may be pulse-modulated at a selected duty-cycle. In some embodiments the power delivered to neighboring electrodes in a set is synchronized, so that power is not supplied simultaneously to neighboring electrodes in the same set, to prevent undesired interferences between neighboring electrodes.

According to some embodiments the device further comprises a gas composition monitor, configured to monitor the gas composition inside the chamber during plasma generation. The device may be associated with a controller configured to achieve and maintain a desired level (a desired concentration) of a specific gas species in the chamber during plasma generation. The controller may further be associated with a plasma governing knob, configured to vary plasma operating conditions. Thus, the controller may receive from the gas composition monitor a continuous signal indicating the momentary concentrations of one or more gas species, compare the measured concentration to the desired concentration of the gas, and command to vary one or more plasma governing knobs to achieve and maintain the desired concentration of the specific gas.

According to an aspect of the invention there is further provided a device for disinfecting herbs using a disinfection agent. The device comprises a main chamber defining a space configured to contain the herbs, the main chamber being configured to be sealingly closed. The device further comprises a perforated carrier configured to contain the herbs during the disinfection process, and to allow penetration of gas though the carrier's walls and floor. The device further comprises a pumping gas port fluidly associated with a valve and with the main chamber and configured to fluidly associate the main chamber with a vacuum pump via the valve. The device further comprises one or more evaporation chambers configured to receive therein a disinfection agent in a liquid form and to evaporate the disinfection agent by heat, each evaporation chamber being fluidly associated with the main chamber via a channel configured to direct a disinfecting gas comprising the vapor of the disinfection agent from the evaporation chamber to the main chamber. The device further comprises at least one electrode associated with each channel and configured to electrically associate to an EM power source and to apply a plasma-generating EM field within the channel, upon receiving a suitable EM power from the power source. And The device further comprises a screen positioned inside the main chamber between the openings of the channels in the main chamber and the perforated carrier, being thereby configured to divert the flow of the disinfecting gas as it enters the main chamber from the channels.

According to an aspect of the invention the device may be used by loading the herbs into the perforated carrier in the sealable chamber; sealingly closing the chamber and evacuating the chamber to a pressure of about 1-100 mbar; releasing a disinfecting gas into the chamber via the channel so as to increase the pressure in the chamber to about 10-500 mbar; using the screen positioned between openings of the channel in the chamber and the perforated carrier to divert the gas flowing into the chamber, thereby enhancing a more uniform distribution of the disinfecting gas in the chamber; generating plasma in the channel by supplying EM power to the electrodes and applying a plasma-generating EM field; ventilating the chamber by air to reach an atmospheric pressure therein, and opening the chamber and dislodging the herbs from the carrier.

Certain embodiments of the present invention may include some, all, or none of the above advantages. Further advantages may be readily apparent to those skilled in the art from the figures, descriptions, and claims included herein. Aspects and embodiments of the invention are further described in the specification hereinbelow and in the appended claims.

Unless otherwise defined, all technical and scientific terms used herein have the same meaning as commonly understood by one of ordinary skill in the art to which this invention pertains. In case of conflict, the patent specification, including definitions, governs. As used herein, the indefinite articles "a" and "an" mean "at least one" or "one or more" unless the context clearly dictates otherwise.

BRIEF DESCRIPTION OF THE FIGURES

Some embodiments of the invention are described herein with reference to the accompanying figures. The description, together with the figures, makes apparent to a person having ordinary skill in the art how some embodiments of the invention may be practiced. The figures are for the purpose of illustrative discussion and no attempt is made to show structural details of an embodiment in more detail than is necessary for a fundamental understanding of the invention. For the sake of clarity, some objects depicted in the figures are not to scale.

In the Figures.

DETAILED DESCRIPTION OF SOME EMBODIMENTS

The principles, uses and implementations of the teachings herein may be better understood with reference to the accompanying description and figures. Upon perusal of the description and figures present herein, one skilled in the art is able to implement the teachings herein without undue effort or experimentation.

Figure 1:
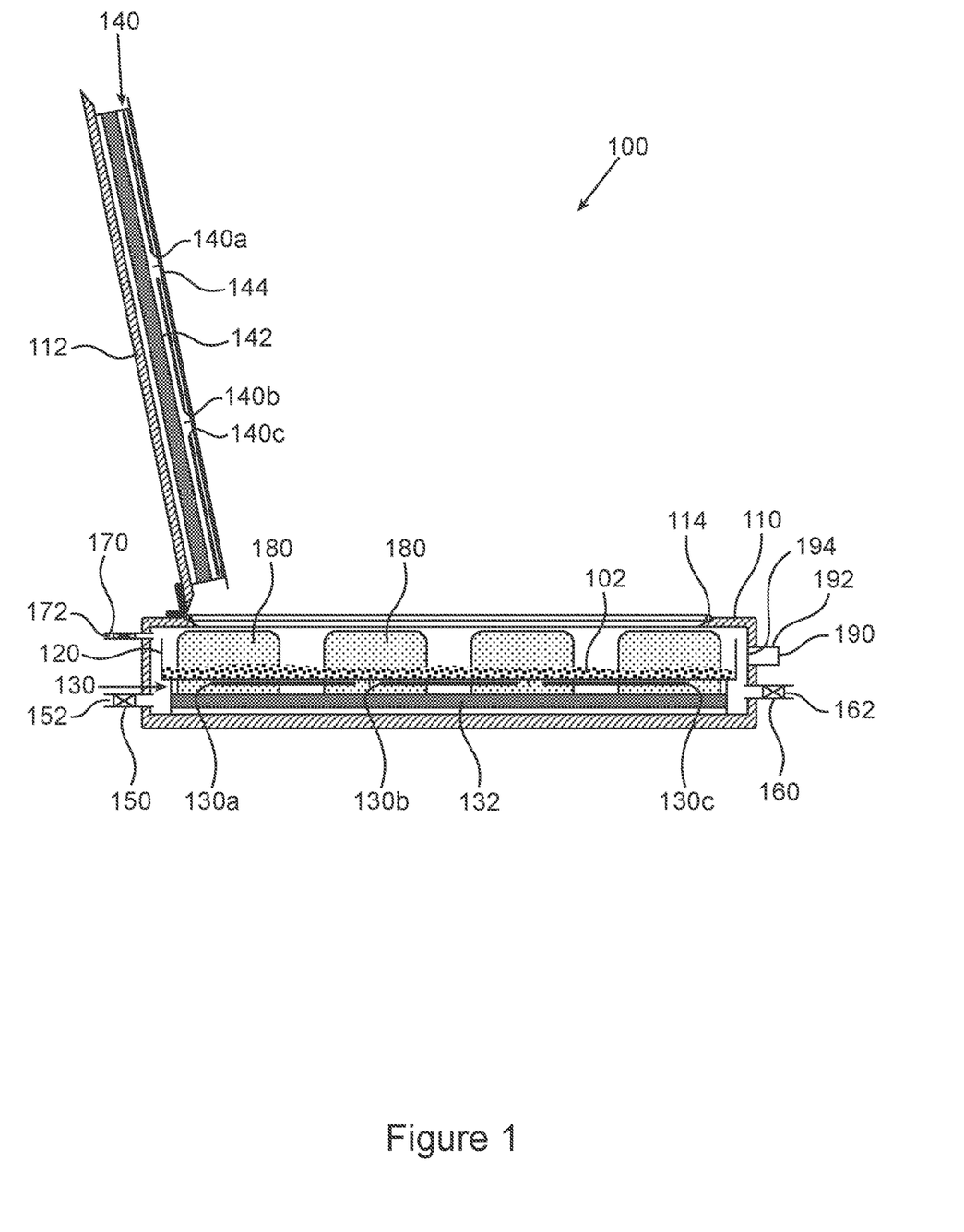
FIG. 1 schematically depicts an embodiment of a device for disinfecting herbs using plasma, according to an aspect of the invention.

FIG. 1 schematically depicts an embodiment of a device 100 for disinfecting herbs 102 according to an aspect of the invention. Device 100 comprises a closable chamber 110 in a shape of a box having a door 112. The chamber may be sealed by a seal 114 when the door is closed. The door is preferably located on the top face of the box, to allow easy loading and easy removing of the herbs into and from the chamber. The device further comprises a carrier 120 configured to contain the herbs during treatment. The carrier may be in the form of a tray with vertical edges or in the form of a basket, and may preferably be made of a dielectric material resilient to the active atmosphere present in the chamber during plasma generation, possibly a polymer and preferably glass or quartz. The carrier 120 may preferably—but should not necessarily—be portable, namely detachable from the chamber. A portable carrier may allow loading the herbs into the carrier away from the chamber, thereby preventing or limiting scatter of debris in the chamber.

The device further comprises a bottom set of electrodes 130, comprising one or more electrodes 130a, 130b, 130c etc., located underneath the carrier. The electrodes are aligned along a plane parallel to the floor of the carrier wherein each electrode may be shaped as a planar sheet having a simple boundary such as a rectangular or triangular or hexagonal or a rounded boundary. Alternatively each electrode may be shaped as an elongated flat stripe, possibly curved, or a group of stripes electrically connected together, shaped and arranged to be bounded within an area of a simple boundary as described above.

The device may further comprise a bottom insulator 132 located between the electrodes 130 and the bottom wall of the chamber, configured to prevent current leakage or arcing between the electrodes and the chamber. Accordingly, insulator 132 may be considerably thicker than the floor of carrier 120.

The device further comprises a top set of electrodes 140, comprising one or more electrodes 140a, 140b, 140c etc., positioned along a plane parallel to the inner face of door 112 and detached from the door. The electrodes 130 and 140 are positioned and aligned in pairs wherein the electrodes in each pair faces each other when the door is closed and sealed, so that electrode 130a faces electrode 140a, electrode 130b faces electrode 140b and so on. In this position, when the door 112 is closed during operation, each pair of electrode is configured to produce a plasma-generating electromagnetic (EM) field in the space between the electrodes.

The device may further comprise a top insulator 142 located between the electrodes 140 and the door, configured to prevent current leakage or arcing between the electrodes and the chamber. Similarly to insulator 132, top insulator 142 may be considerably thicker than the floor of carrier 120. According to some embodiments the device may further comprise a top insulating layer 144, positioned so as to be between the electrodes 140 and the carrier 120 when the door is closed, and configured to provide a dielectric barrier between the top electrodes and the treated material.

The pairs of electrodes are configured to connect to corresponding electric power sources (not shown here), such sources being configured for providing radio-frequency (RF) high voltage (HV) power to the electrodes. According to some embodiments, each pair of electrodes is electrically isolated from the other pairs, so that voltage is supplied to the pair, and a plasma-generating field is produced between the electrodes of the pair, independently of the voltage supply to the other pairs and the corresponding plasma generation by the other pairs. According to some embodiments, some or all of the electrodes in the set of electrodes 130 are electrically connected together, and correspondingly some or all of the electrodes in the set of electrodes 140 are electrically connected together, so that a single power source may supply HV to several electrode pairs simultaneously.

According to some embodiments the electrodes have a non-planar face on the side facing the treated material. According to some embodiments, the bottom electrodes, or the top electrodes or both sets of electrodes may comprise sharp protrusions such as needles pointing towards the treated space, so as to generate a stronger field in the vicinity of the needle tips of the electrode, and hence facilitate plasma ignition.

According to some embodiments the power supplied to the electrode pairs may be modulated, preferably pulse modulated, at a pre-defined duty cycle. According to some embodiments, overall power regulation of the plasma treatment may be controlled using the duty cycle of the pulsed power supplied to the electrodes, rather than using the voltage. It should be noted that ionizable gas is a field-dependent load for the HV power supply, and plasma ignition and generation has a complex dependency on the voltage of the plasma-generating electric field over different plasma regimes. In other words, varying the voltage may yield a qualitatively different behavior of the plasma, resulting in substantial load variations. In contrast, varying the duty cycle of a pulsed power supply has a small or even vanishing effect on the nature of the plasma and hence the load, and thus allows a linear regulation of the average power delivered to the plasma, over a wide range of power levels.

Device 100 further comprises a pumping gas port 150, controlled by a pumping valve 152, configured to fluidly associate with a vacuum pump (not shown here) for pumping the interior of the chamber and reduce the air pressure therein prior to and during operation. According to some embodiments, the pressure in the chamber during operation and plasma generation is below 20 mbar, or below 10 mbar, or below 2 mbar or even below 1 mbar.

In addition to evacuating the chamber prior to the plasma (disinfection) process, pumping may be used in some embodiments also to remove from the chamber gaseous residues of the plasma prior to opening the chamber. In other words, residues of the plasma excitation that are relatively stable may preferably be removed in a controlled manner and not released to the room atmosphere upon opening the chamber. To this end, a suitable filter or a trap (not shown here) may be used at the pumping port. For example, an Ozone filter may be used to filter out residues of Ozone; a vapor trap may be used to condensate residues of vaporized H2O2; and so on. Thus a sequence of steps comprising ventilating the chamber and evacuating the chamber via the pumping port, that may be employed once or several times, may be carried out following the plasma treatment and prior to opening the chamber, to safely remove all dangerous species through a dedicated filtration system and prevent releasing such plasma residues to the ambient.

Device 100 may further comprise an inlet gas port 160, controlled by an input valve 162, configured to fluidly associate to a pressurized gas source (not shown here) for controllably allowing a gas into the chamber. Such a gas that is released into the chamber may possibly be an inert gas such as helium or argon, or a gas such as nitrogen, and additionally or alternatively a potentially active gas such as oxygen. According to some embodiments, the chamber may be pumped via pumping port 150, and flushed with a gas from the pressurized gas reservoir (gas source) via inlet port 160, until the atmosphere inside the chamber reaches a desired composition, at a desired overall pressure (which may be similar or lower than one atmosphere as described above).

According to some embodiments device 100 comprises a leak port 170 controlled by a leak valve 172, the leak port being configured to allow controlled leakage of air from the ambient into the chamber, typically during operation. Such leakage may be used e.g. for stirring the low-pressure gas inside the chamber during operation, thereby mobilizing the gas across regions of the chamber and enhancing uniformity of treatment across the chamber.

Device 100 may comprise, according to some embodiments, transparent inspection windows 180 on the chamber walls, allowing a user inspection of the glow discharge inside the chamber during operation. According to some embodiments the device may further include a pressure gauge (not shown here) inside the chamber for monitoring the pressure during operation. According to some embodiments, activating or allowing HV supply to the electrodes may be carried out only when the pressure inside the chamber has reached a pre-defined level. The device may further comprise a temperature sensor (not shown here) for monitoring or measuring the temperature inside the chamber during operation.

According to some embodiments, device 100 comprises a gas composition monitor 190, configured to monitor the gas composition inside the chamber 110 during plasma generation. According to some embodiments gas composition monitor 190 may be a spectrometer 192 configured to collect light emitted from the excited gas in the chamber through a transparent view port 194 (e.g. a window or an optical fiber) during plasma generation. According to some embodiments, spectrometer 192 may carry out a wide spectrum measurement of the light emitted by the excited gas, using e.g. a diffraction technique by utilizing for example a prism or a diffraction grating. The spectrometer may in such embodiments provide information on the presence and possibly also on the amounts or relative concentrations of a variety of gas species in the gaseous composition in the chamber, according to the distinctive emission patterns of such gas species. According to some embodiments, the spectrometer may be configured to measure the collected light intensity, only in a narrow band of the spectrum, for example by utilizing a narrow band pass filter in front of a light intensity detector. The pass band of the filter may be selected to fit the emission peak of a particular gas species, the abundance of which in the composition is desired to be measured. A suitable calibration process may be carried out to calibrate the amplitude of a light signal associated with the emission of a particular gas species, with the relative concentration of this species in the gas composition in the chamber.

Some gas species, particularly reactive species and radicals, are known to be more instrumental than others for microbial disinfection. Some such gas species are O, OH and OOH, all believed to have half-life time much shorter than a second. Moreover, the prevalence of any particular gas species may vary in time during plasma excitation due to the destructive and constructive effects on a single molecule type the EM field and the excited molecules around have. In other words, once plasma is ignited in a space containing an initial gaseous composition, it should be expected that the initial composition will not remain unchanged, but that the gas composition would change in time. Furthermore, the details of such variances in composition may depend on materials in the chamber—in particular the treated material—that are exposed to the plasma. For example, it may be expected that two different samples of treated herbs containing different levels of moisture, may effect different levels of hydrogen-containing molecules in the excited gas composition. Further yet, a desired level of particular gas species may not be reached in the chamber, unless such gas species or a precursor material for which is presented into the chamber. For example, a desired level of O radicals may not be reached in the chamber, unless O2 gas is released into the chamber during plasma excitation. Likewise, a desired level of OH or H2O2 may be attained by introducing into the chamber controlled amounts of e.g. water vapor or H2O2, or other materials that may compose or decompose in the excited atmosphere to assist in the prevalence of such desired molecule.

It may thus be advantageous to continuously monitor one or more such gas species so as to maintain its abundance in the excited gas composition within desired levels. According to some embodiments, device 100 may be associated with a controller (not shown in FIG. 1) so that the controller is configured to achieve and maintain a desired level (a desired concentration) of a specific gas species in the chamber during plasma generation. The controller may receive from gas composition monitor 190 a continuous signal indicating the momentary concentrations of one or more gas species, and compare the measured concentration to the desired concentration of the gas species. The gas composition monitor may also be used to monitor a precursor to the desired gas. For example, a humidity sensor in the chamber may be used to monitor the amount of water vapor in the chamber, that may contribute to the prevalence of hydrogen-containing molecules, as described above. In some embodiments, two gas concentration monitors may be used, that may employ different technologies, for example a humidity sensor to monitor moisture level, and a spectrometer to monitor free radicals concentrations.

The controller may further be associated with a plasma governing knob (not shown here), configured to vary the plasma operating conditions. Such a plasma governing knob may include for example a valve controlling the release into the chamber of a selected material, e.g. water vapor, or H2O2 vapor, or a gas such as oxygen or nitrogen or an inert gas such as argon or helium. Additionally or alternatively the plasma governing knob may control one or more of the parameters of the plasma generating EM field, for example amplitude (field strength), frequency, pulse width, duty cycle etc. By continuously monitoring the actual gas concentration in the chamber, and commanding to vary one or more plasma governing knobs while implementing a feedback algorithm, a desired level of the gas concentration may be achieved and maintained during the plasma generation.

According to some embodiments disinfection treatment of herbs in Device 100 can be carried out when the herbs are stored in a dielectric container, thereby facilitating handling the herbs, namely introducing the herbs to the device and removing the herbs from the device after treatment. A particular advantage of using such a container is avoiding exposure of the herbs to ambient conditions, hands or tools and other potential sources of contamination, after the treatment. According to some such embodiments, a container equipped with a unidirectional valve as is further detailed below, may be evacuated in the chamber 110 of device 100 while the chamber is evacuated, and may be removed from the chamber after treatment, wherein the herbs there inside having been disinfected, stored in vacuum and possibly ready for shipment. Such a container may in some embodiments be rigid and configured to maintain its shape under a pressure of 1 atmosphere after evacuation. According to some embodiments, such a container may be soft, as described herein below.

Figures 2A, 2B:
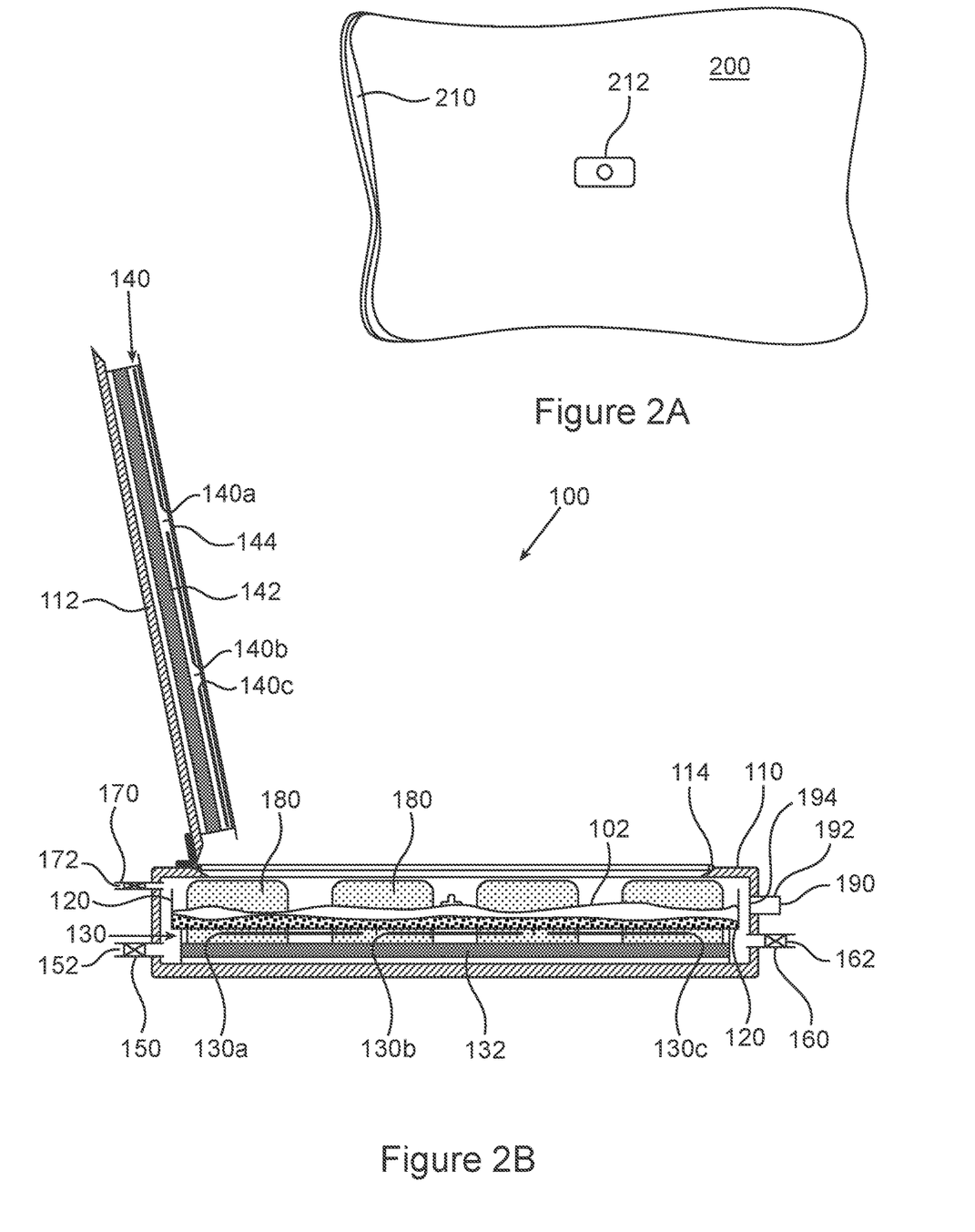
FIG. 2A schematically depicts an embodiment of a soft container shaped as a bag and configured to store the herbs thereinside during plasma treatment.
FIG. 2B schematically depicts the soft container of FIG. 2A filled with herbs, in the device of FIG. 1, and FIG. 3 schematically depicts an embodiment of a device for disinfecting herbs using a disinfection agent, according to an aspect of the invention.

FIG. 2A schematically depicts a soft container 200 shaped as a bag and configured to store the herbs 102 thereinside during plasma treatment. Soft container 200 may be made of a dielectric material such as soft plastic or Nylon. Soft container 200 comprises a sealable opening 210, for inserting and exerting the herbs into and out from the soft container. After inserting the herbs into the soft container, sealable opening 210 may be sealed so as not to allow gas, and particularly biological contaminants from the ambient, into the soft container. Sealable opening 210 may be configured for a single use, so that opening the bag prevents its further use. Alternatively, sealable opening 210 may be configured for multiple use, allowing opening the bag after sealing, and sealing the bag after opening.

Soft container 200 further comprises a unidirectional valve 212, configured to allow gas flow from the soft container outside, and not to allow any flow of gas from the outside into the soft container.

For use, soft container 200, filled with herbs 102, may be placed in device 100 as schematically depicted in FIG. 2B, on carrier 120, prior to treatment. After door 112 closes, the interior of chamber 110 may be evacuated to a pre-defined sub-atmospheric pressure, whereas soft container 200 is concurrently evacuated also via unidirectional valve 212. After the pressure in the chamber has reached a desired level, the pressure inside the soft container is substantially equal to the pressure in the chamber, and plasma may be activated. It should be understood that when plasma is generated in the chamber between electrodes 130 and 140, plasma is generated in particular within soft container 200. After treatment the chamber may be aired, whereas the soft container remains sealed, and the herbs inside remain stored under vacuum.

Figure 3:
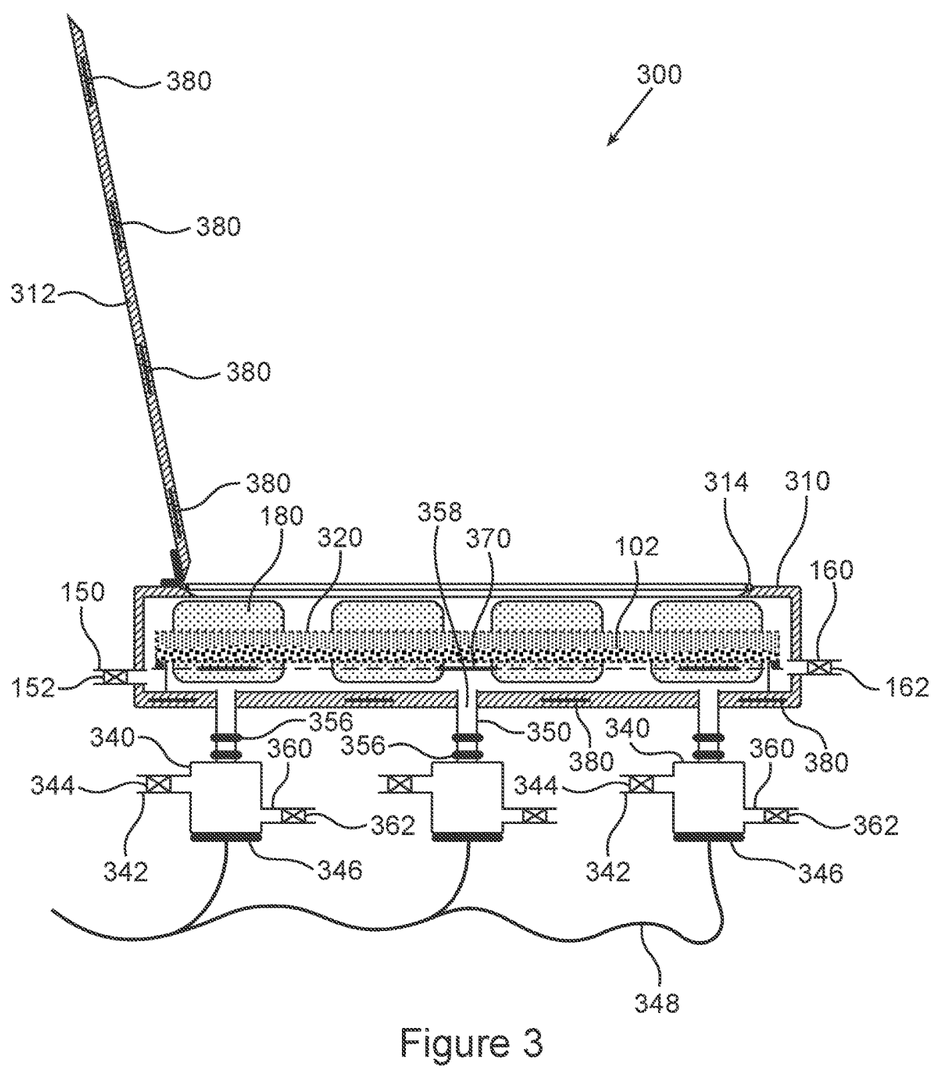

FIG. 3 schematically depicts an embodiment of a device 300 for disinfecting herbs 102 according to an aspect of the invention. Device 300 comprises a closable main chamber 310 in a shape of a box having a door 312. The main chamber may be sealed by a seal 314 when the door is closed. The door is preferably located on the top face of the box, to allow easy introduction and easy removing of the herbs to and from the main chamber. Device 300 is different from device 100 in several aspects. According to one such aspect, device 300 is configured to disinfect herbs using the indirect plasma scheme. According to another aspect, it is configured to disinfect herbs without plasma at all. Consequently, and for clarity of the description, device 300 is depicted here without electrodes 130 and 140. However it is emphasized that in some embodiments, a device for disinfecting herbs is contemplated, that includes all the features of device 300 and any of the features of device 100, and vice versa—a device is for disinfecting herbs is contemplated that includes all the features of device 100 and any of the features of device 300.

Device 300 comprises a carrier 320 configured to contain the herbs during treatment. The carrier may be in the form of a tray with vertical edges or in the form of a basket, and may preferably be perforated, to facilitate diffusion or flow of gases into and out from the carrier. Carrier 320 may be made of a material resilient to the active atmosphere present in the chamber during the disinfection process, possibly metal or a polymer and preferably stainless steal, glass or quartz.

According to some embodiments, disinfection in device 300 is carried out using a disinfection agent in the form of a gas. According to some embodiments the gas may be flowed into the chamber via inlet gas port 160. According to some embodiments, the disinfecting gas may be obtained by evaporating a liquid, as is described herein below. Possible evaporating disinfection agents may include—but are not limited to—hydrogen peroxide (H2O2), Ethylene Oxide (ETO) and paracetic acid, for example.

For evaporating a disinfection agent, device 300 comprises one or more evaporation chambers 340. Each evaporation chamber is fluidly associated with a disinfection agent port 342, equipped with a valve 344 configured to control inflow of a disinfection agent into the evaporation chamber, the disinfection agent port being fluidly connected to a disinfection agent source (not shown here). It will be understood by the person skilled in the art that in some embodiments a central valve—rather than a valve associated with each disinfection agent port—may control the inflow of the disinfection agent.

Each evaporation chamber is thermally coupled with a heater 346 configured to heat the evaporation chamber and the disinfection agent there inside to cause evaporation, preferably to a temperature above the boiling point of the disinfection agent liquid. For example, the boiling temperature of hydrogen peroxide is about 150 deg.C; but hydrogen peroxide is often provided and used mixed with water, and the boiling temperatures of 30%, 50% and 70% H2O2 solutions are about 107 deg.C, 113 deg.C and 125 deg.C, respectively. For heating, the heaters 346 may be electrically connected 348 to a heater power source (not shown here) which may be controlled to supply EM power to the heaters to effect the heating.

The evaporation chambers are advantageously made of a durable material configured to withstand possible corrosion by the disinfection agent at boiling temperatures. For hydrogen peroxide, a metallic chamber may be used, made for example of aluminum or stainless steel.

According to some embodiments the evaporated disinfecting gas may be excited to plasma en route between the evaporation chamber 340 and the main chamber 310. According to some embodiments, channels 350, e.g. in the form of tubes, as depicted in FIG. 3, fluidly connect each evaporation chamber 340 to the main chamber 310, so that vapor of the disinfection agent may diffuse or flow into the main chamber via channel openings 358.

According to some embodiments, the vapor may be excited to plasma by high voltage (HV) electromagnetic (EM) power. The HV EM power may be supplied to electrodes 356 which are configured to apply a plasma-generating EM field in the electrodes vicinity, e.g. inside the channels. It should be understood that electrodes suitable for applying such a plasma-generating EM field may be configured in one of many shapes and configurations. The electrodes 356 depicted in FIG. 3, for example, are arranged as two cylindrical electrodes, arranged externally, and detached from one another, on each tube, wherein the plasma-generating EM field is applied in the space substantially between the electrodes. Other configurations are contemplated as well. According to some embodiments, a single cylindrical electrode may be used, whereas the plasma-generating EM field may be applied in this case in the space substantially between the single electrode and a grounded metal part of the device, for example main chamber 310. According to some embodiments the electrodes may be internal to the tubes. According to some embodiments a helical electrode, wrapped around the tube, may be used. According to some embodiments, the HV EM power supplied to the electrodes may be at radio frequency (RF). The tubes may preferably be made of a dielectric material such as a polymer, glass or quartz, so that the tube walls do not screen the EM field, and allow simple generation of plasma inside the tubes.

According to some embodiments each evaporation chamber is fluidly associated with an air inlet port 360 configured to allow air into the main chamber 310 via the evaporation chambers 340. An air inlet valve 362 fluidly associated with the air inlet port 360 may control the inflow of air. It will be understood by the person skilled in the art that in some embodiments a central valve—rather than a valve associated with each air inlet port—may be fluidly associated to several air inlet ports and control the inflow of air through all of them.

According to some embodiments the main chamber 310 comprises a ramp 370, on which the carrier 320 is placed during operation. Ramp 370 extends substantially along the entire area of the carrier, underneath the carrier, and may be partially perforated to allow the disinfecting gas evaporating from the evaporation chamber via channels 350 and via openings 358 to diffuse and flow into the carrier. By partially perforated it is meant that perforations in the ramp are not distributed evenly on the surface of the ramp. The ramp may be more perforated in areas that are distant from the channel openings, and be less perforated, or not perforated at all, in areas close to the channel openings or right above the channel openings, to enhance more uniform distribution of the disinfecting gas in the main chamber.

In operation, device 300 is activated in cycles wherein in each cycle—termed also a session—an amount of herbs 102 is introduced into the main chamber 310, treated for disinfection and then removed from the chamber. Prior to the first session the evaporation chambers may be heated to a desired temperature by heaters 346, so as to expedite evaporation of the disinfection agent during the treatment session. Also, chamber heaters 380 may be used to pre-heat the main chamber walls. According to some embodiments, the chamber walls may be maintained at a temperature above room temperature, to prevent or to decrease condensation of the disinfection agent vapors of the walls. According to some embodiments the chamber walls may be maintained at a temperature between about 30 degC and about 70 degC. The upper temperature limit may be dependent on the type of herbs being treated and the sensitivity of the herbs to high temperature. In some embodiments, therefore, the chamber walls may be maintained at a temperature above room temperature and below 60 deg.C or below 50 deg.C or even below 40 deg.C.

A treatment session may begin by loading a desired amount of herbs to the carrier. The herbs may be loaded in a bulk as depicted in FIG. 3, or within a container—e.g. a rigid container or a soft container. It should be emphasized that in contrast to the soft container depicted in FIGS. 2A and 2B, which is sealed to gases and may only release gas outwards through unidirectional valve 212, a container suitable for use with device 300 must be perforated to allow gas flow into and out from the container.

The carrier 320 may preferably—but should not necessarily—be portable, namely detachable from the main chamber. A portable carrier may allow loading the herbs into the carrier away from the main chamber, thereby preventing or limiting scatter of debris in the main chamber.

The carrier with the herbs loaded therein may be positioned in place in the main chamber, the main chamber may be sealed by closing the door 312 and the chamber may be evacuated through the gas pumping port 150. Evacuation may be carried out to reach a sub-atmospheric pressure, e.g. below 100 mbar or below 10 mbar or even to about 1 mbar. When a desired pressure level in the chamber is reached, pumping gas from the chamber—namely evacuation—stops, e.g. by shutting pumping valve 152.

Following evacuation, a disinfecting gas may be released into the main chamber. As discussed above, such disinfecting gas may be released into the main chamber directly via gas inlet port 160 or by introducing a disinfection agent in a liquid form into evaporation chambers 340. The introduction of the disinfection agent to the pre-heated evaporation chambers generates substantial evaporation—preferably accompanied by boiling of the disinfection agent—and releasing of vapors of the disinfection agent into the main chamber via channels 350. According to some embodiments, electrode or electrodes 356 may be used prior to introduction of the disinfection agent to the evaporation chambers, to generate plasma in the interior of the channels 350, to render the inner surfaces of the walls of the channels hydrophilic. It is noted that increased hydrophilicity of the walls may cause increased wetting of the walls, and hence decreased accumulation of vapor condensate on the walls.

The release of disinfecting gas into the chamber causes, generally, increase in chamber pressure. It is generally desired to reach at least 5 to 10 fold increase in pressure inside the chamber, so that the dominant component in the chamber's atmosphere is the disinfecting gas. Further, when the pressure is increased by way of releasing the disinfecting gas into the chamber, penetration of the disinfecting gas to slits and pores is greatly enhanced. It should be emphasized that herbs are often characterized by very high ratio of surface area to total volume. Herbs in the form of a pile of powder or grinded material, or even in natural forms having intricate structure such as porous bark or inflorescence such as in cannabis, may be considered as examples. Obtaining a uniform concentration of the disinfecting gas by way of only diffusion and concentration equilibrium is generally a very-lengthy process, whereas obtaining a uniform concentration by way of pressure equilibrium is much faster and substantially immediate.

In some embodiments, and particularly when the disinfecting gas is obtained by heating a liquid disinfecting agent, the vapor released from the evaporation chambers tends to condensate on surfaces in the surroundings. Thus the release of vapor into the chamber causes the pressure in the chamber to rise, effecting, in turn, penetration of the vapor to slits and pores, and generally to hardly-accessed locations in the treated material. Then the vapor of the disinfecting agent may condensate on the herbs, effecting a disinfection process. For increased effectiveness, several sequences of chamber evacuation followed by pressure increase via release of a disinfecting gas may be employed.

In some embodiments it is advantageous to promote uniform distribution of the released gas inside the chamber by diverting the gas from channel openings 358, so that the vapors, and resulting condensation, would not concentrate in the surroundings of the channels openings. For this end, ramp 370, positioned substantially between the openings and the carrier 320, may be partially perforated so as to limit the flow of vapors in the areas close to the openings, and enhance flow of vapors towards the carrier in the areas more distant from the openings. Thus, the ramp may be non-uniformly perforated. As an example, uniformly distributed holes the diameters of which are larger as the holes are more distant from the openings may be considered; or perforated according to one of many other arrangements of holes locations and diameters that can achieve the said result.

In some embodiments plasma may be generated in the channels 350 during the release of the disinfecting gas, thereby effecting a disinfection treatment according to the indirect plasma scheme discussed above. According to some such embodiments, excitation of the gas to plasma may generate more excited species or free radicals, that may enhance disinfection. For example, if H2O2 is evaporated in the evaporation chambers and released as a vapor to the main chamber, excitation of the H2O2 vapor to plasma may generate some amount of HO, O3 and possibly NOx (if some native nitrogen is present in the chamber), that may enhance disinfection.

The herbs may be kept immersed in the disinfecting gas for a duration that typically ranges between tens of second and tens of minutes, e.g. between 30 seconds and 30 minutes or even between 5 and 15 minutes. Such duration may include repeating sequences of evacuation and releasing disinfecting gas into the chamber as described above.

In some embodiments a gas composition monitor (190 in FIG. 1) may be used to monitor the gas composition inside the main chamber during the treatment time—namely during the immersion time of the herbs in the disinfecting gas. According to some such embodiments, the gas composition monitor may be installed in the vicinity of one of the channels 350, to monitor the gas composition during plasma generation therein using electrodes 356. In some embodiments, device 300 may comprise one or sets of electrodes 130 and 140 to generate plasma in the main chamber, in which case gas composition monitor 190 may monitor the gas composition in the main chamber. In some such embodiments, a single pair of electrodes—such as for example electrodes 130c and 140c as depicted in FIG. 1—may be activated to generate plasma locally in a limited region within the main chamber, for the sole purpose of gas composition analysis using the gas composition monitor.

Upon monitoring the gas composition within the chamber, a disinfection agent may be added—or not—so as to increase the amount of disinfecting gas in the chamber. In some embodiments, as described above, a controller that receives from the gas composition monitor a signal indicating the momentary concentrations of one or more gas species, may compare the measured amount of the disinfecting gas to a desired amount set by a user, and accordingly command—or not—to open valve 342 to introduce more disinfection agent to the evaporation chamber.

Following the immersion period, the main chamber may be ventilated by releasing air into the chamber. In some embodiments air may be allowed into the chamber via the air inlet ports 360. By streaming the air into the chamber via the evaporation chambers, remains of the vapors of the disinfection agent may be removed from the chamber more effectively. According to some embodiments, ventilation of the chamber may be accompanied by evacuating the chamber by pumping. As explained above, in relation to FIG. 1, removing from the chamber residues of the disinfecting gas by pumping may be particularly advantageous over releasing such residues directly to the ambient by opening the chamber, because such residues may be trapped or filtered at the pumping port or between the pumping port and the vacuum pump, or at the outlet of the vacuum pump. For example, for preventing release of vaporized H2O2 to the ambient, a vapor trap may be used to condensate the vapors and collect the condensate for safe removal.

Prior to ventilating the chamber, or in parallel to the sequence of ventilating and evacuating the chamber as described above, plasma may be generated in the channels 350 to expedite dissociation of active species to stable molecules. For example, plasma may be generated to expedite the dissociation of H2O2 in the chamber's atmosphere, so as to minimize release of H2O2 vapor to the ambient, and to minimize H2O2 residues on the treated herbs.

There is thus provided according to an aspect of the invention a device 100 for disinfecting herbs 102 using plasma. The device comprises chamber 110 defining a space configured to contain the herbs. The device further comprises at least two sets of opposing electrodes 130 and 140, respectively, each set comprising one or more electrodes 130*a*, 130*b* etc., and 140*a*, 140*b*, etc. Each two opposing electrodes, e.g. 130*a* and 140*a*, are associated with a power source configured to supply to the electrodes RF HV for producing a plasma-generating EM field between the electrodes. The device further comprises carrier 120 made of a dielectric material shaped as a tray having a floor and up-straight walls and configured to contain the herbs on the carrier's floor. The device further comprises gas composition monitor 190 configured to monitor an amount or relative occurrence (portion) of a gas in the gaseous composition in the chamber. The gas composition monitor is associated with a controller, the controller being configured to compare the monitored amount or relative occurrence of gas to a pre-defined amount or relative occurrence of gas provided by a user. The amount or relative occurrence may be at least one selected from the group consisting of partial pressure, molality, mole fraction, mole ratio, mass fraction, mass ratio, mass concentration, molar concentration, and number concentration.

According to some embodiments the gas composition monitor collects light emitted from the plasma in the chamber. According to some embodiments the gas composition monitor comprises a light diffracting component. According to some embodiments the gas composition monitor comprises a spectral filter. According to some embodiments the gas composition monitor comprises a humidity sensor.

According to some embodiments the gas is at least one selected from the group consisting of O, OH, OOH, H2O, H2O2, O3, NOx, He and Ar.

According to some embodiments the controller is configured to command a variation in a plasma operational parameter, to achieve or to maintain equality between said monitored amount of gas to said pre-defined amount of gas provided by the user. According to some embodiments the plasma operational parameter is at least one selected from the group consisting of amount of a precursor released into the chamber, pressure in the chamber, EM field frequency, EM field strength, EM field modulation pulse width, and EM field modulation duty cycle. According to some embodiments the controller is associated with a plasma governing knob configured to affect a plasma operational parameter variation.

According to an aspect of the invention there is further provided a method for disinfecting herbs using plasma. The method comprises providing soft container 200 made substantially of a flexible dielectric sheet impermeable to gas and equipped with sealable opening 210 and with unidirectional valve 212. The method further comprises loading the soft container with the herbs, sealing the soft container at the sealable opening and placing the sealed container in the carrier 120 of the device 100. The method further comprises evacuating the chamber of the device, thereby evacuating the soft container via the unidirectional valve. The method further comprises applying a plasma-generating EM field between the electrodes 130 and 140, by supplying to the electrodes a suitable EM power, thereby generating plasma in the space between the electrodes and particularly inside the soft container. The method further comprises ventilating the chamber with air and opening the chamber, thereby rendering the herbs sealed within the soft container, in vacuum.

There is further provided according to an aspect of the invention device 300 for disinfecting herbs. The device comprises main chamber 310 defining a space configured to contain the herbs, the main chamber being configured to be sealingly closed. The device further comprises perforated carrier 320 configured to contain the herbs during the disinfection process, and to allow penetration of gas though the carrier's walls and floor. The device further comprises pumping gas port 150 fluidly associated with valve 152 and with the main chamber and configured to fluidly associate the main chamber with a vacuum pump via the valve. The device further comprises one or more evaporation chambers 340 configured to receive therein a disinfection agent in a liquid form and to evaporate the disinfection agent by heat. Each evaporation chamber is fluidly associated with the main chamber via channel 350 configured to direct a disinfecting gas comprising the vapor of the disinfection agent from the evaporation chamber to the main chamber. The device further comprises at least one electrode 356 associated with each channel and configured to electrically associate to an EM power source and to apply a plasma-generating EM field within the channel, upon receiving a suitable EM power from the power source. And the device further comprises screen 370 positioned inside the main chamber between openings 358 of the channels in the main chamber and the perforated carrier, being thereby configured to divert the flow of the disinfecting gas as it enters the main chamber from the channels.

According to some embodiments the device further comprises one or more air inlet ports 360, fluidly associating the ambient with each evaporation chamber via valve 362.

According to some embodiments each evaporation chamber is thermally coupled with heater 346 configured to heat the evaporation chamber's walls to evaporate the disinfection agent there inside. According to some embodiments the disinfection agent is selected from the group consisting of H2O2, ETO and paracetic acid.

According to some embodiments the carrier 320 is portable, enabling to load the carrier with herbs and to dislodge the herbs from the carrier away from the main chamber.

According to some embodiments the main chamber walls are thermally associated with chamber heaters 380 configured to maintain the chamber's walls at a temperature higher than room temperature to minimize condensation of vapors of the disinfection agent on the chamber's walls.

According to some embodiments the device 300 further comprises a gas composition monitor 190 configured to monitor an amount or relative portion of a gas in the gaseous composition in the chamber. According to some embodiments the gas composition monitor is associated with a controller, the controller being configured to compare the monitored amount or relative portion of gas to a pre-defined value provided by a user.

There is further provided according to an aspect of the invention a method for disinfecting herbs 102. The method comprises loading the herbs into a perforated carrier 320 in a sealable chamber 310 fluidly associated with a vacuum pump. The perforated carrier is configured to carry the herbs and to allow penetration of gas through the perforations in the carrier's walls and floor. The method further comprises sealingly closing the chamber and evacuating the chamber to a pressure of about 1-100 mbar. The method further comprises releasing a disinfecting gas into the chamber via a channel 350 so as to increase the pressure in the chamber to about 10-500 mbar. The method further comprises using a screen 370 positioned between openings of the channel in the chamber and the perforated carrier to divert the gas flowing into the chamber, thereby enhancing a more uniform distribution of the disinfecting gas in the chamber. The method further comprises generating plasma in the channel by applying a plasma-generating EM field. The method further comprises ventilating the chamber by air to reach an atmospheric pressure therein. And the method further comprises opening the chamber and dislodging the herbs from the carrier.

According to some embodiments the plasma generation is performed before the step of releasing a disinfecting gas into the chamber via a channel. Such plasma generation renders the inner surfaces of the channel walls hydrophilic and prevents or limits vapor condensation on the channel's walls. According to some embodiments the plasma generation is performed during the step of releasing a disinfecting gas into the chamber via a channel. According to some embodiments the plasma generation is performed after the step of releasing a disinfecting gas into the chamber via a channel and before the step of ventilating the chamber by air to reach an atmospheric pressure therein.

According to some embodiments the method comprises more than one sequence of the steps of evacuating the chamber to a pressure of about 1-100 mbar and releasing a disinfecting gas to the chamber to reach a pressure of about 10-500 mbar.

According to some embodiments the step of releasing a disinfecting gas into the chamber is carried out by releasing a disinfection agent in a liquid form to an evaporation chamber fluidly associated with the main chamber via the channel, and evaporating the disinfection agent inside the evaporation chamber by heat.

According to some embodiments the step of ventilating the chamber is carried out by releasing air into the evaporation chamber. According to some embodiments the method comprises more than one sequence of the steps of evacuating the chamber and ventilating the chamber by air prior to opening the chamber. According to some embodiments the method comprises within the sequence of steps of evacuating the chamber and ventilating the chamber also a step of generating plasma in the channel by applying a plasma-generating EM field.

According to some embodiments the method further comprises maintaining the chamber walls at a temperature between room temperature and 70 DegC, or 60 Deg.C or 50 Deg.C or 40 Deg.C, to reduce vapor condensation on the walls.

It is appreciated that certain features of the invention which are described in the context of separate embodiments, may also be provided in combination in a single embodiment. For example, the plasma generating electrodes 130 and 140, or the gas composition monitor 190, or any other components that are described in FIG. 1, may be employed in the disinfection device of FIG. 3; and vice versa—disinfecting using a disinfection agent, with or without employing evaporation chambers as described in FIG. 3, may be used in the disinfection device of FIG. 1. Moreover, various features of the invention, which are described in the context of a single embodiment, may also be provided separately or in any suitable sub-combination or as suitable in any other described embodiment of the invention. No feature described in the context of an embodiment is to be considered an essential feature of that embodiment, unless explicitly specified as such.

Although steps of methods according to some embodiments may be described in a specific sequence, methods of the invention may comprise some or all of the described steps carried out in a different order. A method of the invention may comprise all of the steps described or only a few of the described steps. No particular step in a disclosed method is to be considered an essential step of that method, unless explicitly specified as such.

Although the invention is described in conjunction with specific embodiments thereof, it is evident that numerous alternatives, modifications and variations that are apparent to those skilled in the art may exist. Accordingly, the invention embraces all such alternatives, modifications and variations that fall within the scope of the appended claims. It is to be understood that the invention is not necessarily limited in its application to the details of construction and the arrangement of the components and/or methods set forth herein. Other embodiments may be practiced, and an embodiment may be carried out in various ways.

The phraseology and terminology employed herein are for descriptive purpose and should not be regarded as limiting. Citation or identification of any reference in this application shall not be construed as an admission that such reference is available as prior art to the invention. Section headings are used herein to ease understanding of the specification and should not be construed as necessarily limiting.

The invention claimed is:

1. A method for disinfecting herbs, the method comprising:
    loading the herbs into a perforated carrier in a sealable chamber fluidly associated with a vacuum pump, the perforated carrier being configured to carry the herbs and allow penetration of gas through the perforations in the carrier's walls and floor;
    sealingly closing the chamber and evacuating the chamber to a pressure of about 1-100 mbar;
    releasing a disinfecting gas into the chamber via at least one channel so as to increase the pressure in the chamber to about 10-500 mbar;
    prior to releasing a disinfecting gas, generating plasma in the channel by applying a plasma-generating electromagnetic (EM) field, thereby rendering the inner surfaces of the channel walls hydrophilic and preventing or limiting vapor condensation on the channel's walls;
    ventilating the chamber by air to reach an atmospheric pressure therein; and
    opening the chamber and dislodging the herbs from the carrier.

2. The method of claim 1 wherein the releasing a disinfecting gas into the chamber is carried out by releasing a disinfection agent in a liquid form to an at least one evaporation chamber fluidly associated with the main chamber via the at least one channel, and evaporating the disinfection agent inside the evaporation chamber by heat.

3. The method of claim 2 wherein the ventilating the chamber is carried out by releasing air into the at least one evaporation chamber.

4. The method of claim 1, further comprising using a screen positioned between the opening of the at least one channel in the chamber and the perforated carrier to divert the gas flowing into the chamber, thereby enhancing a more uniform distribution of the disinfecting gas in the chamber.

5. The method of claim 1, wherein a sequence including of evacuating the chamber to a pressure of about 1-100 mbar and releasing a disinfecting gas to the chamber to reach a pressure of about 10-500 mbar is repeated sequentially at least once.

6. The method of claim 5 wherein the sequence includes, prior to releasing a disinfecting gas to the chamber, generating plasma in the channel by applying a plasma-generating EM field.

7. The method of claim 1, further comprising maintaining the chamber walls at a temperature between room temperature and 70° C., 60° C., 50° C., or 40° C., to reduce vapor condensation on the walls.

8. A method for disinfecting herbs, the method comprising:
- loading the herbs into a perforated carrier in a sealable chamber fluidly associated with a vacuum pump, the perforated carrier being configured to carry the herbs and allow penetration of gas through the perforations in the carrier's walls and floor;
- sealingly closing the chamber and evacuating the chamber to a pressure of about 1-100 mbar;
- releasing a disinfecting gas into the chamber via at least one channel so as to increase the pressure in the chamber to about 10-500 mbar, while maintaining the chamber walls at a temperature above 40° C., to reduce vapor condensation on the walls;
- generating plasma in the channel by applying a plasma-generating electromagnetic (EM) field;
- ventilating the chamber by air to reach an atmospheric pressure therein; and
- opening the chamber and dislodging the herbs from the carrier.

9. The method of claim 8 wherein the plasma generation is performed before the releasing a disinfecting gas into the chamber via a channel, thereby rendering the inner surfaces of the channel walls hydrophilic and preventing or limiting vapor condensation on the channel's walls.

10. The method of claim 8 wherein the plasma generation is performed during the releasing a disinfecting gas into the chamber via a channel.

11. The method of claim 8 wherein the plasma generation is performed after the releasing a disinfecting gas into the chamber via a channel and before the ventilating the chamber by air to reach an atmospheric pressure therein.

12. The method of claim 8 wherein the releasing a disinfecting gas into the chamber is carried out by releasing a disinfection agent in a liquid form to an at least one evaporation chamber fluidly associated with the main chamber via the at least one channel, and evaporating the disinfection agent inside the evaporation chamber by heat.

13. The method of claim 12 wherein the ventilating the chamber is carried out by releasing air into the at least one evaporation chamber.

14. The method of claim 8, further comprising using a screen positioned between the opening of the at least one channel in the chamber and the perforated carrier to divert the gas flowing into the chamber, thereby enhancing a more uniform distribution of the disinfecting gas in the chamber.

15. The method of claim 8, wherein a sequence including of evacuating the chamber to a pressure of about 1-100 mbar and releasing a disinfecting gas to the chamber to reach a pressure of about 10-500 mbar is repeated sequentially at least once.

16. The method of claim 15 wherein the sequence includes, prior to releasing a disinfecting gas to the chamber, generating plasma in the channel by applying a plasma-generating EM field.

* * * * *